(12) United States Patent
Kaiser

(10) Patent No.: US 9,040,082 B2
(45) Date of Patent: *May 26, 2015

(54) COMPOSITIONS AND METHODS FOR TREATMENT OF CHRONIC FATIGUE

(75) Inventor: Jon D. Kaiser, Mill Valley, CA (US)

(73) Assignee: K-PAX Pharmaceuticals, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 13/530,673

(22) Filed: Jun. 22, 2012

(65) Prior Publication Data

US 2012/0328695 A1 Dec. 27, 2012

Related U.S. Application Data

(60) Provisional application No. 61/500,869, filed on Jun. 24, 2011.

(51) Int. Cl.
| | |
|---|---|
| A61K 9/48 | (2006.01) |
| A01N 43/90 | (2006.01) |
| A61K 31/522 | (2006.01) |
| A01N 43/40 | (2006.01) |
| A61K 31/445 | (2006.01) |
| A61K 31/44 | (2006.01) |
| A01N 43/26 | (2006.01) |
| A61K 31/385 | (2006.01) |
| A01N 43/04 | (2006.01) |
| A61K 31/70 | (2006.01) |
| A61K 45/06 | (2006.01) |
| A61K 31/4415 | (2006.01) |
| A61K 31/4458 | (2006.01) |
| A61K 31/714 | (2006.01) |

(52) U.S. Cl.
CPC ............. *A61K 31/385* (2013.01); *A61K 45/06* (2013.01); *A61K 31/4415* (2013.01); *A61K 31/4458* (2013.01); *A61K 31/522* (2013.01); *A61K 31/714* (2013.01)

(58) Field of Classification Search
CPC . A61K 45/06; A61K 31/385; A61K 31/4415; A61K 31/4458; A61K 31/522; A61K 31/714; A61K 2300/00; C07G 13/00
USPC ............................. 424/451; 514/263.31, 317
See application file for complete search history.

(56) References Cited

U.S. PATENT DOCUMENTS

| | | |
|---|---|---|
| 4,542,123 A | 9/1985 | Wurtman |
| 5,096,712 A | 3/1992 | Wurtman |
| 5,895,652 A | 4/1999 | Giampapa |
| 5,916,912 A | 6/1999 | Ames et al. |
| 5,948,443 A | 9/1999 | Riley et al. |
| 6,063,820 A | 5/2000 | Cavazza |
| 6,103,756 A | 8/2000 | Gorsek |
| 6,191,162 B1 | 2/2001 | Byrd et al. |
| 6,284,767 B1 | 9/2001 | Sham et al. |
| 6,300,377 B1 | 10/2001 | Chopra |
| 6,365,622 B1 | 4/2002 | Cavazza |
| 6,423,349 B1 | 7/2002 | Sherratt et al. |
| 6,451,341 B1 | 9/2002 | Slaga et al. |
| 6,458,384 B2 | 10/2002 | Jaenicke et al. |
| 6,479,069 B1 | 11/2002 | Hamilton |
| 6,541,043 B2 | 4/2003 | Lang |
| 6,579,544 B1 | 6/2003 | Rosenberg et al. |
| 6,733,797 B1 | 5/2004 | Summers |
| 6,845,777 B2 | 1/2005 | Pera |
| 6,964,969 B2 | 11/2005 | McCleary |
| 7,250,181 B2 | 7/2007 | Ghosal |
| 7,489,964 B2 | 2/2009 | Suffin et al. |
| 7,560,100 B2 | 7/2009 | Pinchasi et al. |
| 7,585,523 B2 | 9/2009 | Shell et al. |
| 7,601,369 B2 | 10/2009 | Shell et al. |
| 7,645,742 B2 | 1/2010 | Stohs |
| 7,776,915 B2 | 8/2010 | Morariu |
| 7,893,070 B2 | 2/2011 | van Kempen |
| 7,962,204 B2 | 6/2011 | Suffin et al. |
| 7,968,125 B2 | 6/2011 | Henderson et al. |
| 7,976,879 B2 | 7/2011 | Roizen |
| 8,187,647 B2 | 5/2012 | Bhargava |
| 8,202,525 B2 | 6/2012 | Crain et al. |

(Continued)

FOREIGN PATENT DOCUMENTS

| | | |
|---|---|---|
| WO | WO-94/02036 A1 | 2/1994 |
| WO | WO-99/43329 | 9/1999 |

(Continued)

OTHER PUBLICATIONS

Carruthers et al (2003) "Myalgic Encephalomyelitis/Chronic Fatigue Syndrome." Journal of Chronic Fatigue Syndrome, 11(1): 7-115.*

(Continued)

*Primary Examiner* — Anoop Singh
*Assistant Examiner* — Doan Phan
(74) *Attorney, Agent, or Firm* — Dickstein Shapiro LLP

(57) ABSTRACT

Pharmaceutical compositions and methods for the treatment of chronic fatigue in human patients comprising a central nervous system (CNS) stimulant in a daily low-dosage amount in combination with therapeutically effective daily amounts of micronutrients, comprising acetyl L-carnitine, L-tyrosine, N-acetyl cysteine, and alpha-lipoic acid. The CNS and micronutrient components may be in an oral dosage composition containing a low dosage amount of CNS stimulant such as about 2.5 mg methylphenidate HCl together with about 60-250 mg acetyl L-carnitine, 50-200 mg L-tyrosine, 60-250 mg N-acetyl cysteine, and 25-100 mg alpha-lipoic acid.

13 Claims, 4 Drawing Sheets

(56) References Cited

U.S. PATENT DOCUMENTS

| | | | |
|---|---|---|---|
| 8,224,433 | B2 | 7/2012 | Suffin et al. |
| 2001/0031744 | A1 | 10/2001 | Kosbab |
| 2002/0155163 | A1 | 10/2002 | Benjamin et al. |
| 2002/0176900 | A1 | 11/2002 | Yegorova |
| 2002/0182196 | A1* | 12/2002 | McCleary ............... 424/94.1 |
| 2003/0068391 | A1 | 4/2003 | Harris et al. |
| 2003/0147975 | A1 | 8/2003 | Joshi et al. |
| 2003/0206895 | A1 | 11/2003 | Cavazza |
| 2004/0077556 | A1 | 4/2004 | Chinery |
| 2004/0157783 | A1 | 8/2004 | McCaddon |
| 2005/0058672 | A1 | 3/2005 | Gupta |
| 2006/0112584 | A1 | 6/2006 | Jones |
| 2006/0257502 | A1 | 11/2006 | Liu |
| 2007/0166408 | A1 | 7/2007 | Shell et al. |
| 2007/0197663 | A1 | 8/2007 | Epstein et al. |
| 2007/0237834 | A1 | 10/2007 | Gupta |
| 2008/0038409 | A1 | 2/2008 | Nair et al. |
| 2008/0207757 | A1 | 8/2008 | Mickle |
| 2008/0213397 | A1 | 9/2008 | Kaiser |
| 2008/0213401 | A1 | 9/2008 | Smith |
| 2009/0239949 | A1 | 9/2009 | Mickle |
| 2009/0325999 | A1 | 12/2009 | Du |
| 2010/0080863 | A1 | 4/2010 | Sommerfeld et al. |
| 2010/0331274 | A1 | 12/2010 | Gupta et al. |
| 2011/0033506 | A1 | 2/2011 | Penhasi et al. |
| 2011/0077194 | A1 | 3/2011 | McCaddon |
| 2011/0110913 | A1 | 5/2011 | Grant et al. |
| 2011/0159048 | A1 | 6/2011 | Crain et al. |
| 2012/0164243 | A1 | 6/2012 | Rinsch et al. |
| 2012/0237570 | A1 | 9/2012 | Crain et al. |
| 2012/0328695 | A1 | 12/2012 | Kaiser |

FOREIGN PATENT DOCUMENTS

| | | |
|---|---|---|
| WO | WO-00/11968 A1 | 3/2000 |
| WO | WO-00/67596 | 11/2000 |
| WO | WO-00/76492 A1 | 12/2000 |
| WO | WO0126642 A2 * | 4/2001 |
| WO | WO-03/037320 A1 | 5/2003 |
| WO | WO-2005/000203 A2 | 1/2005 |
| WO | WO 2005/067972 A1 | 7/2005 |
| WO | WO-2010/015029 A1 | 2/2010 |

OTHER PUBLICATIONS

D. Blockmans et al., "Does Methylphenidate Reduce the Symptoms of Chronic Fatigue Syndrome?," The American Journal of Medicine, vol. 119, pp. 167.e23-167.e30, 2006.

ABC News Report—"Some Supplement—Medication Combinations Make Dangerous Mix," http://abcnews.go.com/Health/We... News/supplements-make-dangerous-mix/story?did=12133148.

D.G. Meyers et al., "Safety of Antioxidant Vitamins," Archives of Internal Medicine, vol. 156, No. 9, pp. 925-935, May 13, 1996, Abstract.

P. Gardiner et al., "Factors Associated with Dietary Supplement Use Among Prescription Medication Users," Arch. Intern. Med., vol. 166, pp. 1968-1974, Oct. 9, 2006.

FoodFacts from the U.S. Food and Drug Administration, Dietary Supplements, What You Need to Know FDA, pp. 1-2, May 2006.

Essential Nutrients: Food or Supplements? JAMA vol. 294(3): pp. 351-335, 2005, Abstract.

G. Bjelakovic et al., "Mortality in Randomized Trials of Antioxidant Supplements for Primary and Secondary Prevention, Systematic Review and Meta-Analysis ," JAMA, vol. 297, No. 8 pp. 842-857, Feb. 28, 2007.

Letters, JAMA , vol. 299, No. 7, pp. 765-766, Feb. 20, 2008.

D. M. Qato et al., "Use of Prescription and Over-the-Counter Medications and Dietary Supplements Among Older Adults in the United States," JAMA, vol. 300, No. 24, pp. 2867-2878, Dec. 24/31, 2008.

B. M. Carruthers et al., "Myalgic Encephalomyelitis/Chronic Fatigue Syndrome: A Clinical Case Definition and Guidelines for Medical Practitioners," Journal of Chronic Fatigue Syndrome, vol. 11, No. 1, pp. 7-115, An Overview of the Canadian Consensus Document, pp. 1-20, 2003.

M. Cheng, "Study Questions Chronic Fatigue Treatment Methods," SFGate.com, Friday, Feb. 18, 2011, http://www.sfgate.com/cgi-bin/article.cgi?f=/n/a/2011/02/17/international/i60210s57.DTL&type=printable.

Prof. P. D. White, et al., "Comparison of Adaptive Pacing Therapy, cognitive Behaviour Therapy, Graded Exercise Therapy, and Specialist Medical Care for Chronic Fatigue Syndrome (PACE): A Randomised Trial," The Lancet, Early Online Publciation, Feb. 18, 2011. http://www.lancet.com/journals/lancet/article/PIIS0140-6736(11)60096-2.

M. R. Werbach, M.D., "Nutritional Strategies for Treating Chronic Fatigue Syndrome," Alternative Medicine Review, vol. 5 No. 2, pp. 93-108, 2000.

C. K. Joseph, "Nutritional Supplements: Amino Acids and Their Derivatives," American Journal of Pharmaceutical Education, vol. 66, pp. 157-164, Summer, 2003.

L. Isa et al., "Blood Zinc Status and Zinc Treatment in Human Immunodeficiency Virus-Infected Patients," Int. J. Clin. Lab. Res., vol. 22, pp. 45-47, 1992.

M. Malaguarnera et al., "Acetyl L-Carnitine (ALC) Treatment in Elderly Patients with Fatigue," Archives of Gerontology and Geriatrics, pp. 1-10, 2007.

B. V. Houdenhove et al., "Chronic Fatigue Syndrome: Is there a Role for Non-Antidepressant Pharmacotherapy?," Expert. Opin. Pharmacother., vol. 11, No. 2, pp. 215-223, 2010.

J. Ramon et al., "Diagnostic and Treatment Challenges of Chronic Fatigue Syndrome: Role of Immediate-Release Methylphenidate," Expert Rev. Neurother. vol. 8, No. 6, pp. 917-927, 2008.

T. L. Schwartz, MD, "Modafinil Treatment for Fatigue Associated with Fibromyalgia," Journal of Clinical Rheumatology, vol. 13, No. 1, pp. 52, Feb. 2007.

K. Holtorf, "Diagnosis and Treatment of Hypothalamic-Pituitary-Adrenal (HPA) Axis Dysfunction in Patients with Chronic Fatigue Syndrome (CFS) anf Fibromyalgia," Journal of Chronic Fatigue Syndrome, vol. 14, No. 3, pp. 1-14, 2008.

Dr. Jacob Teitelbaum, "Treatment for Chronic Fatigue Syndrome," ImmuneSupport.com, pp. 1-14, Apr. 28, 2004, retrieved from internet Sep. 4, 2012, http://www.immunesupport.com/chronic-fatigue-syndrome-treatment.htm> entire document.

Dr. Charles Lapp, M.D., "Effective Treatment of Chronic Fatigue Syndrome and Fibromyalgia," ProHealth, Oct. 9, 2002. http://www.prohealth.com/library/print.cfm?libid-8801.

Supplementary European Search Report dated Aug. 13, 2008.

Patrick, "Nutrients and HIV: Part Three—N-Acetylcysteine, Alpha-Lipoic Acid, L-Glutamine, and L-Carnitine," (Altern Med Rev 2000, 5(4), 290-305).

Patrick, Nutrients and HIV: Part 2—Vitamins A and E, Zinc, B-Vitamins, and Magnesium, (Altern Med Rev 2000, 5(1), 39-51).

Nijveldt et al., "Flavonoids: a review of probable mechanisms of action and potential applications[1-3]," (Am J Clin Nutr 2001, 74, 418-25).

Fawzi et al., "A Randomized Trial of Multivitamin Supplements and HIV Disease Progression and Mortality," (N. Engl. J. Med 2004, 361, 23-32).

Kaiser et al., "Micronutrient Supplementation Increases CD4 Count in HIV-Infected Individuals on Highly Active Antiretroviral Therapy: A Prospective, Double-Blinded, Placebo-Controlled Trial," (J Acquir Immune Defic Sydr 2006, 42(5), 523-528).

Abbas et al. "Evaluation of the efficacy of thiamine and pyridoxine in the treatment of symptomatic diabetic peripheral neuropathy," *East Afr. Med. J.* 74(12):803-808 (1997).

Allard et al., "Effects of vitamin E and C supplementation on oxidative stress and viral load in HIV-infected subjects," *Aids* 12(13):1653-1659 (1998).

Aukrust et al., "Glutathione redox disturbances in human immunodeficiency virus infection: immunologic and therapeutic consequences," *Nutrition* 15(2)165-167 (1999).

Baur et al., "Alpha-lipoic acid is an effective inhibitor of human immuno-deficiency virus (HIV-1) replication," *Klin. Wochenschr.* 69(15):722-724 (1991).

(56) References Cited

OTHER PUBLICATIONS

Bernstein et al., "Brief communication: effect of pharmacologic doses of vitamin B6 on carpal tunnel syndrome, electroencephalographic results, and pain," *J. Am. Coll. Nutr.* 12(1):73-76 (1993).

Buhl et al., "Systemic glutathione deficiency in symptom-free HIV-seropositive individuals," *Lancet* 334(8675): 1294-8 (1989).

Buttke et al., "Oxidative stress as a mediator of apoptosis," *Immunol. Today* 15(1):7-10 (1994).

Campos et al., "Plasma carnitine insufficiency and effectiveness of L-carnitine therapy in patients with mitochondrial myopathy," *Muscle Nerve* 16(2): 150-153 (1993).

Chen et al., "Delayed cytotoxicity and selective loss of mitochondrial DNA in cells treated with the anti-human immunodeficiency virus compound 2',3'-dideoxycytidinne," *J. Biol. Chem.* 264(20):11934-11937 (1989).

Chen et al., "Effect of anti-human immunodeficiency virus nucleoside analogs on mitochondrial DNA and its implication for delayed toxicity," *Mol. Pharmacol.* 39(5):625-628 (1991).

Choi et al., "Molecular mechanism of decreased glutathione content in human immunodeficiency virus type 1 Tat-transgenic mice," *J. Biol. Chem.* 275(5):3693-3698 (2000).

Dalakas et al., "Zidovudine-induced mitochondrial myopathy is associated with muscle carnitine deficiency and lipid storage," *Ann. Neurol.* 35(4):482-487 (1994).

De Quay et al., "Glutathione depletion in HIV-infected patients: role of cysteine deficiency and effect of oral N-acetylcysteine," *AIDS* 6(8):815-819 (1992).

Douglas Laboratories, Inc. "Energizer Formula—Nutritional Support for Mitochondrial Energy Production" (1999).

Famularo et al., "Acetyl-carnitine deficiency in AIDS patients with neurotoxicity on treatment with antiretroviral nucleoside analogues," *AIDS* 11(2):185-190 (1997).

Famularo et al., Letter to the Editor, *Comment on Scarpini et al.* "Effect of acetyl-L-carnitine in the treatment of painful peripheral neuropathies in HIV+ patients," *J. Peripher. Nerv. Syst.* 3(3):227-229 (1998).

Fuchs et al., "Studies on lipoate effects on blood redox state in human immunodeficiency virus infected patients," *Arzneimittelforschung* 43(12):1359-1362 (1993).

Herzenberg et al., "Glutathione deficiency is associated with impaired survival in HIV disease," *Proc. Natl. Acad. Sci. USA* 94(5):1967-1972 (1997).

Kaiser, M.D., Jon D., Healing HIV How to Rebuild Your System, Health First Press, Mill Valley, California (1999).

Kalebic et al., "Suppression of human immunodeficiency virus expression in chronically infected monocytic cells by glutathione, glutathione ester, and N-acetylcysteine," *Proc. Natl. Acad. Sci. USA* 88(3):986-990 (1991).

Khouri et al., Lactic acidosis secondary to nucleoside analog antiretroviral therapy, *Infec. Med.* 17(8):541-554 (2000).

Kuby, Immunology, 3rd Edition, W.H. Freeman & Co., New York (1997).

Packer et al., "Vitamin E and alpha-lipoate: role in antioxidant recycling and activation of the NF-kappa B transcription factor," *Mol. Aspects Med.* 14(3):229-239 (1993).

Parker et al., "Mitochondrial toxicity of antiviral nucleoside analogs," *J. NIH Res.* 6:57-61 (1994).

Paul, W.E., Fundamental Immunology, 2nd Edition, Raven Press, New York (1989).

Sato et al., "Thiol-mediated redox regulation of apoptosis. Possible roles of cellular thiols other than glutathione in T cell apoptosis," *J. Immunol.* 154(7):3194-3203 (1995).

Scarpini et al., "Effect of acetyl-L-carnitine in the treatment of painful peripheral neuropathies in HIV+patients," *J. Peripher. Nerv. Syst.* 2(3):250-252 (1997).

Shor-Posner et al, "Neuroprotection in HIV-positive drug users: implications for antioxidant therapy," *J. Acquir. Immune Defic. Syndr.* 31 Suppl 2:S84-S88 (2002).

Simpson et al., "Neurologic manifestations of HIV infection," *Ann. Intern. Med.* 121(10):769-785 (1994). Review. Erratum in: *Ann. Intern. Med.* 122(4):317 (1995).

Thorne Research, Inc., "Do You Care About What You Put in Your Body?," http://www.thorne.com/index/mod/rs/a/rs.

UF News, "UF Researcher Finds Vitamins and Exercise May Slow the Harmful Effects of Aging," http://www.napa.ufl.edu/2003news/vitamine.htm (2003).

Witschi et al., "The systemic availability of oral glutathione," *Eur. J. Clin. Pharmacol.* 43(6):667-669 (1992).

Ziegler et al., "Alpha-lipoic acid in the treatment of diabetic peripheral and cardiac autonomic neuropathy," *Diabetes* 46 Suppl 2:S62-S66 (1997).

Ziegler et al., "Alpha-lipoic acid in the treatment of diabetic polyneuropathy in Germany: current evidence from clinical trials," *Exp. Clin. Endocrinol. Diabetes* 107(7):421-430 (1999).

A. M. Hart et al., "Acetyl-Carnitine: a pathogenesis based treatment for HIV-associated antiretroviral toxic neuropaty," *AIDS* 2004, vol. 18: pp. 1549-1560.

G. McComsey et al., "Effect of Antioxidants on Glucose Metabolism and Plasma Lipids in HIV-Infected Subjects with Lipoatrophy," Journal of Acquired Immune Deficiency Syndromes, vol. 33, pp. 605-607.

S. Moretti et al., "Effect of L-Carnitine on Human Immunodeficiency Virus-1 Infection-Associated Apoptosis: A Pilot Study," Blood, vol. 91, No. 10, pp. 3817-3824, May 15, 1998.

H. M. Coovadia et al., "Zinc deficiency and supplementation in HIV/AIDS," Nutrition Research, vol. 22, Issue 1, pp. 179-191, Jan. 2002.

F. Gutierrez et al., "Patients characteristics and clinical implications of suboptimal CD4 T-cell gains after 1 year of successful antiretroviral therapy," Curr. HIV Res., Mar. 2008, 6(2): 100-7, Abstract.

A. Hanna et al., "A Phase II Study of Methylphenidate for the Treatment of Fatigue." Support Care Cancer, vol. 14, pp. 210-215, 2006.

* cited by examiner

COMPOSITIONS AND METHODS FOR TREATMENT OF CHRONIC FATIGUE

This application claims the benefit of U.S. Provisional Application Ser. No. 61/500,869, filed Jun. 24, 2011.

FIELD OF THE INVENTION

This disclosure relates to pharmaceutical compositions and methods for the treatment of chronic fatigue, including Chronic Fatigue Syndrome (CFS) and chronic fatigue associated with other conditions, such as fibromyalgia, cancer, AIDS, chronic hepatitis B & C, autoimmune disorders, Lyme's disease, Parkinson's disease, Alzheimer's disease, psychological disorders including depression, attention deficit disorder (ADD), and attention deficit hyperactivity disorder (ADHD), multiple sclerosis, sickle cell anemia, and congestive heart failure. In particular, provided herein are pharmaceutical compositions and treatment regimes utilizing a combination of a low dose central nervous system (CNS) stimulant with a group of high potency nutrients, the strategic combination of which provides significantly improved outcomes for patients experiencing chronic fatigue.

BACKGROUND

CFS, also known as Chronic Fatigue and Immune Dysfunction Syndrome (CFIDS) or Myalgic Encephalomyelitis (ME), is a disorder characterized by overwhelming chronic fatigue of greater than six months duration that is not improved by rest and may be worsened by physical or mental activity. Patients with CFS typically function at a significantly lower level of activity than they were capable of before the onset of illness.

CFS patients commonly report various symptoms including weakness, muscle pain, post-exertional fatigue lasting more than 24 hours, impaired memory and/or mental concentration, depression, and insomnia. These symptoms are often made worse by being tired and in pain the majority of one's waking hours. The immune system is frequently dysfunctional in patients experiencing chronic fatigue syndrome, and consequently many patients with CFS also experience frequent sore throats, colds, and flu-like symptoms. Benign lymphadenopathy can also occur in some patients. Other commonly observed symptoms of CFS include: abdominal pain, alcohol intolerance, bloating, chest pain, headaches, chronic cough, diarrhea, dizziness, dry eyes or mouth, ear aches, irregular heartbeat, jaw pain, morning stiffness, nausea, night sweats, psychological problems (depression, irritability, anxiety, and/or panic attacks), shortness of breath, skin sensations such as tingling, and weight loss.

The cause or causes of CFS have not been identified. CFS is a profoundly multifactorial condition. However, its myriad symptoms profile has been traced to a dis-integration of neurologic, endocrine, and immune system cooperation, possibly attenuated by dysfunction of the hypothalamic-pituitary-adrenal hormonal axis.

To be diagnosed with. CFS, patients typically satisfy two criteria: (1) significant to severe fatigue for at least six months (herein referred to as "chronic fatigue"), with other known medical conditions (whose manifestation can include fatigue) having been excluded by clinical diagnosis; and (2) concurrently four or more of the following symptoms: post-exertional malaise, impaired memory or concentration, unrefreshing sleep, muscle pain, multiple joint pains without redness or swelling, tender cervical or auxiliary lymph nodes, sore throat, and headache, such symptoms having persisted or recurred during six or more consecutive months of illness and not having predated the fatigue. It has been estimated that about 1% of the population in the United States has been diagnosed with CFS.

No prescription drugs have been developed specifically for CFS. The symptoms usually vary considerably over time and among patients. These factors can complicate the treatment process and typically require patients and health care professionals to constantly monitor and revise their treatment strategies. Current therapies for treating CFS primarily focus on attempts at relieving the most debilitating symptoms (i.e., pain, insomnia, and depression). Currently there are no United States Food and Drug Administration ("FDA")-approved or generally accepted treatments that significantly improve or cure CFS.

Similarly, "fibromyalgia" is a condition that includes an overlapping list of symptoms with CFS and frequently includes fatigue, chronic musculoskeletal pain, chronic flu-like symptoms, depression, and cognitive dysfunction. Fibromyalgia is predominately characterized by widespread muscular pains and fatigue.

Fibromyalgia also is characterized by abnormal pain processing, sleep disturbance, chronic fatigue, and is often accompanied by significant psychological distress. Patients experiencing fibromyalgia may also have other symptoms, including morning stiffness, tingling or numbness in the hands and feet, headaches, including migraines, irritable bowel syndrome, problems with thinking and memory (sometimes called "brain fog"), painful menstrual periods, and other pain syndromes. The prevalence of fibromyalgia in the United States is estimated at 2%, affecting 5 million adults in 2005. The prevalence is much higher among women than men (3.4% versus 0.5%) (Female: Male ratio 7:1).

Lyrica (pregabalin capsules) is approved by the FDA for the treatment of fibromyalgia. Fibromyalgia also is commonly treated with a variety of drugs developed and approved for other purposes, such as analgesics, non-steroidal anti-inflammatory drugs (NSAIDS), antidepressants, tricyclic antidepressants, selective serotonin reuptake inhibitors (SSRIs), mixed reuptake inhibitors, and benzodiazepines.

Chronic fatigue may also be caused by other medical conditions. These include, among others, cancer, AIDS, chronic hepatitis B & C, autoimmune disorders, Lyme's disease, Parkinson's disease, Alzheimer's disease, psychological disorders including depression, attention deficit disorder (ADD), and attention deficit hyperactivity disorder (ADHD), multiple sclerosis, sickle cell anemia, and congestive heart failure. In the United States, 24% of the general population has had fatigue lasting 2 weeks or longer; 59%-64% of these persons report that their fatigue has no identifiable medical cause. In one study, 24% of patients in primary care clinics reported having prolonged fatigue (>1 month). In many persons with prolonged fatigue, the fatigue persists beyond 6 months and has no identifiable medical cause.

Accordingly, a significant need exists for compositions and methods for the treatment of chronic fatigue for patients suffering from CFS, fibromyalgia, chronic fatigue caused by or associated with dis-integration of the neuro-endocrine-immune axis, and chronic fatigue caused by other medical conditions. The present disclosure is intended to satisfy this need and is believed to provide significant advantages in patient health care where chronic fatigue is a major symptom.

SUMMARY

The compositions and treatment regimes discussed herein comprise a combination of a low dose central nervous system (CNS) stimulant with a highly-potent group of four specific nutrients for the treatment of CFS, and chronic fatigue associated with other serious medical conditions (such as fibromyalgia, cancer, AIDS, chronic hepatitis B & C, autoimmune disorders, Lyme's disease, Parkinson's disease, Alzheimer's disease, psychological disorders including depression, attention disorder (ADD) and attention deficit hyperactivity disorder (ADHD), multiple sclerosis, sickle cell anemia, and congestive heart failure). The compositions and methods are believed to provide significantly better short and long term patient outcomes from chronic fatigue than the use of current treatment regimes.

In one aspect, the present disclosure provides oral dosage compositions for the treatment of chronic fatigue, such compositions including a central nervous system stimulant in a therapeutically effective low-dosage amount, about 60 to 250 mg acetyl L-carnitine, about 50 to 200 mg L-tyrosine, about 60 to 250 mg N-acetyl cysteine, and about 25 to 100 mg alpha-lipoic acid.

In another aspect, the present disclosure provides methods for treating chronic fatigue in a human patient by administering a daily low-dosage amount of a central nervous system stimulant and therapeutically effective daily dosages of acetyl L-carnitine, L-tyrosine, N-acetyl cysteine, and alpha lipoic acid. In a preferred embodiment, the daily administration includes a micronutrient stimulant component of about 1400 mg to 1600 mg acetyl L-carnitine, and about 350 mg to 1400 mg L-tyrosine; and an antioxidant micronutrient component of about 250 mg to 1250 mg N-acetyl cysteine, and about 150 mg to 600 mg alpha-lipoic acid.

In yet another aspect, the present invention provides methods of treating CFS and chronic fatigue associated with other medical conditions in a human patient by orally administering on a daily basis a central nervous system stimulant in a low-dosage amount, about 100 mg to 2000 mg acetyl L-carnitine, about 1000 mg to 2000 mg L-tyrosine; about 100 mg to 2000 mg N-acetyl cysteine, and about 50 mg to 1000 mg alpha-lipoic acid. The micronutrient antioxidant component may further comprise, for example, L-taurine (such as, about 50 to 1000 mg, 100 to 500 mg, or 200 to 400 mg).

The central nervous system stimulant may be any suitable CNS medication, including, but not limited to, methylphenidate, dexmethylphenidate, modafinil, armodafinil, amphetamines, and atomoxetine HCl, among others, so long as a therapeutically effective low dosage amount is provided as discussed herein, and as may be determined by one of skill in the art given the examples and teachings provided by way of illustration herein.

In one aspect, the compositions and treatment methods utilize a low dosage amount of CNS medicament, together with therapeutically effective amounts of acetyl L-carnitine, L-tyrosine, N-acetyl cysteine, and alpha-lipoic acid, combined together in a pill, capsule, tablet, or liquid dosage form for oral ingestion. For example, for methylphenidate HCl the composition of one pill, tablet, capsule, or liquid dosage form would typically contain about 0.75 to 7.5 mg, 1.25 to 5 mg, or 2 to 3 mg methylphenidate HCl, but may contain other amounts of methylphenidate HCl. Similarly for modafinil or armodafinil, the composition would typically contain about 4 to 40 mg, 6 to 25 mg, or 10 to 20 mg modafinil or armodafinil, but may contain other amounts. For dexmethylphenidate HCl the composition would typically contain about 0.5 to 5 mg, 0.6 to 3 mg, or 0.2 to 2 mg, but may contain other amounts of dexmethylphenidate HCl. For amphetamines, the composition would typically contain 1 to 10 mg, 1.2 to 6 mg, or 0.4 to 4 mg amphetamines, but may contain other amounts. For atomoxetine HCl the composition would typically contain 2 to 20 mg, 3 to 18 mg, or 5 to 10 mg, but may contain other amounts of atomoxetine HCl. For caffeine the composition would typically contain about 15 to 200 mg, 30 to 125 mg, or 50 to 100 mg, but may contain other amounts of caffeine. Such compositions and methods may also be provided, or administered simultaneously, with a broad-spectrum multivitamin and multimineral supplement, or in admixture therewith in a dosage form for ingestion on a daily basis to cure or significantly mitigate chronic fatigue.

Thus, the preferred embodiments rely, at least in part, on relatively low doses of CNS stimulant medications. No study to date has shown that CNS stimulant intervention can produce a sustained beneficial effect on the long-term experience and prognosis for patients with chronic fatigue or CFS. Further, even when medications are successfully prescribed to address certain CFS symptoms, the vast majority of CFS patients achieve less than complete improvement with regular relapses of the condition being the norm.

DETAILED DESCRIPTION OF PREFERRED EMBODIMENTS

Figure 1:
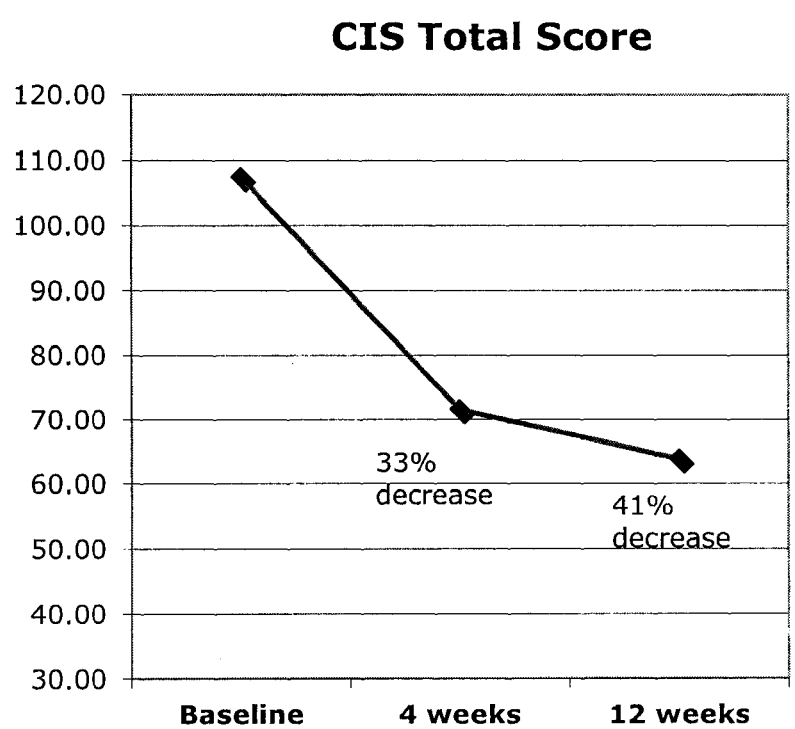
FIG. 1 illustrates patient fatigue as measured by Checklist Individual Strength (CIS) over time according to one aspect of the compositions and methods disclosed herein.

When the cells of the nervous, endocrine, and immune systems become depleted of energy after prolonged periods of stress and/or infection, a disruption of the balance among these systems can occur. This disruption of neurologic, endocrine, and immune system cooperation (possibly attenuated by dysfunction of the hypothalamic-pituitary-adrenal hormonal axis) is believed to be the prevailing etiology of CFS. The resulting symptom profiles almost always contain a significant level of chronic fatigue and/or chronic pain, and often vary from patient to patient.

While not wishing to be bound by theory, it is believed that treating patients suffering from profoundly depleted and weakened nervous and endocrine systems solely with a standard dosage of a CNS stimulant over-stimulates an already worn out nervous system and, at best, might produce a fleeting improvement while, at worst, leads to a significant degradation of the patient's underlying condition. Thus, to date, no treatment regime has been proven to consistently enhance the energy level of patients with CFS (or chronic fatigue due to fibromyalgia, cancer, AIDS, chronic hepatitis B & C, autoimmune disorders, Lyme's disease, Parkinson's disease, Alzheimer's disease, psychological disorders including depression, ADD and ADHD, multiple sclerosis, sickle cell anemia, or congestive heart failure) in a fashion superior to placebo.

Provided herein are compositions and methods utilizing a low dosage of a CNS stimulant in combination with certain high-potency micronutrients. The high potency micronutrient components provide the cellular fuel (amino acids, antioxidants, and mitochondrial cofactors) that enable the nervous, endocrine, and immune system cells to rebuild and reintegrate into a functional neuro-endocrine-immune axis, while the low-dose CNS stimulant provides the necessary catalyst (i.e., spark) to enhance and fuel this process over time. In other words, the high-potency micronutrient components support and enhance the functioning of the nervous, immune, and endocrine systems to a level at which the drug is able to produce its positive clinical effect on the chronic fatigue symptoms without causing further depletion or degradation of these systems.

It is believed that the specific combined micronutrients and amounts discussed herein together with the low dose CNS stimulant medication have synergistic effects and provoke a reintegration of the nervous, endocrine, and immune systems in a significant number of patients with long-standing chronic fatigue or CFS, significantly diminishing or mitigating fatigue symptoms, and allowing at least a significant subset of patients to return to and/or maintain functional work status.

With regard to the CNS stimulant component of the compositions and treatment methods herein, in most cases using the manufacturer's recommended dosage range of a CNS stimulant will not be successful and/or will be detrimental for the long-term treatment of patients suffering from chronic fatigue. While not wishing to be bound by theory, it is believed that the main reason for this is that such patients have nervous and endocrine systems that can be described as "burnt out;" consequently, fatigue, pain, and depression are three highly prevalent symptoms in CFS patients.

Particular examples of suitable CNS medications that may be used herein include, but are not limited to, methylphenidate HCl (e.g., RITALIN®, DAYTRANA®, CONCERTA®, METADATE®, METHYLIN™), dexmethylphenidate HCl (e.g., FOCALIN®), modafinil (e.g., PROVIGIL®), armodafinil (e.g., NUVIGIL®), amphetamines (e.g., ADDERALL®, VYVANSE®), guanfacine (e.g., INTUNIV™), atomoxetine HCl (e.g., STRATTERA®), and pharmaceutically acceptable salts and derivatives thereof. It should be noted, however, that other central nervous system stimulants may be selected and used according to the teachings, compositions, and methods discussed herein, including, but not limited to, lisdexamfetamine, phentermine, dexamphetamine, dextroamphetamine, pemoline, and caffeine, as well as pharmaceutically acceptable salts and derivatives thereof.

Therapeutically effective dosages of CNS medications for use herein are generally low dosages of the CNS medication. "Low dosage" amount of the CNS medication means a dose of between about 10% to 75%, 15% to 60%, 20% to 50%, or less of the manufacturer's suggested starting dosage. The preferred dose for chronic fatigue and CFS is, in most cases, 50% or less than the manufacturer's recommended dosage (MRD). According to one aspect, illustrative low oral dosage amounts of CNS medications for use herein are provided in Table 1 below.

TABLE 1

1. Methylphenidate HCl (e.g., RITALIN ®, DAYTRANA ®, CONCERTA ®, METADATE ®, METHYLIN ™)
2.5 mg-40 mg per day
(18 mg-72 mg per day is the Manufacturer's recommended dosage range)
2. Modafinil (e.g., PROVIGIL ®)
30 mg-100 mg per day
(200 mg-400 mg per day is the Manufacturer's recommended dosage range)
3. Armodafinil (e.g., NUVIGIL ®)
20 mg-100 mg per day TABLE 1-continued (150 mg-250 mg per day is the Manufacturer's recommended dosage range)
4. Dexmethylphenidate HCl (e.g., FOCALIN ®)
2.5 mg-10 mg per day
(5 mg-20 mg per day is the Manufacturer's recommended dosage range)
5. Amphetamines (e.g., ADDERALL ®, VYVANSE ®)
2.5 mg-20 mg per day
(5 mg-40 mg per day is the Manufacturer's recommended dosage range)
6. Atomoxetine HCl (e.g., STRATTERA ®)
20 mg-50 mg per day
(40 mg-100 mg per day is the Manufacturer's recommended dosage range)
7. Caffeine
50 mg-500 mg per day In one aspect, the CNS medication is administered in oral dosage amounts of about 2.5 to 40 mg/day methylphenidate, about 5 to 20 mg/day methylphenidate, or about 10 to 20 mg/day methylphenidate. In another aspect, the CNS medication is administered in amounts of about 30 to 100 mg/day modafinil, about 30 to 50 mg/day modafinil, or about 40 to 50 mg/day modafinil. In another aspect, the CNS medication is administered in amounts of about 20 to 80 mg/day armodafinil, about 20 to 40 mg/day armodafinil, or about 30 to 40 mg/day armodafinil. In yet another aspect, the CNS medication is administered in amounts of about 2.5 to 10 mg/day dexmethylphenidate, about 2.5 to 5 mg/day dexmethylphenidate, or about 3.5 to 5 mg/day dexmethylphenidate. In yet another aspect, the CNS medication is administered in amounts of about 2.5 to 20 mg/day amphetamine, about 2.5 to 10 mg/day amphetamine, or about 5 to 10 mg/day amphetamine. In yet a further aspect, the CNS medication is administered in amounts of about 20 to 50 mg/day atomoxetine, about 20 to 25 mg/day atomoxetine, or about 22.5 to 25 mg/day atomoxetine, or about 50 to 500 mg/day caffeine, 100 to 400 mg/day caffeine, or about 100 to 300 mg/day caffeine. Two or multiple CNS stimulants can also be included in the same composition or method and the amounts of each reduced proportionally given the teachings herein to obtain an overall low dose CNS amount that is therapeutically effective in combination with the disclosed micronutrients.

With regard to the nutrient components, these include various components, each of which may be categorized as having particular functions in the treatment regime. A first component is micronutrients that stimulate energy production; while not wishing to be bound by theory, we believe that these nutrient stimulants help the CNS drug operate more effectively at the low dosages provided for herein. The second component is micronutrients that provide for a "balanced cooling system" for cells; these micronutrients appear to decrease total free radical load and oxidative stress levels, thus reducing the potential for toxic or other side effects of the CNS medication.

Preferred nutrients for energy production according to the teachings herein include acetyl-L-carnitine and L-tyrosine. In some cases, the energy stimulating micronutrient component may further include vitamin B6 (pyridoxine), and vitamin B12 (methylcobalamin). Preferred nutrients that provide for a restorative and balancing effect include N-acetyl-cysteine, alpha-lipoic acid, and optionally L-taurine. In some cases, the antioxidant micronutrient component may further include vitamin C, vitamin E, and beta-carotene. Other nutrients that provide for a restorative and balancing effect and may optionally be included are zinc and selenium, among others.

Additional optional vitamins and nutrients include mixed tocopherols, vitamin B1 (thiamine), vitamin B2 (riboflavin), niacinamide, calcium pantothenate, choline (bitartrate), inositol, folic acid (folacin), folinic acid, biotin, vitamin D3 (cholicalciferol), calcium, magnesium, iron, iodine, copper, manganese, potassium, chromium, molybdenum, and/or boron.

Thus, the high potency nutrient components suitable for use herein include therapeutically effective amounts of two or more nutrients for energy stimulation (collectively, the "micronutrient stimulant component") and two or more nutrients for decreasing free radical load and oxidative stress levels (collectively, the "micronutrient antioxidant component"). The preferred combinations of nutrient components include, in amounts as discussed herein, at least acetyl-L-carnitine and L-tyrosine for energy production, and N-acetylcysteine together with alpha-lipoic acid and, optionally, L-taurine, for decreasing oxidative stress. Other incidental nutrients may include, for example, various high potency vitamins, minerals, amino acids, antioxidants, cofactors, free radical scavengers, elements or biochemical compounds as discussed hereinbelow.

Suitable daily oral dosages of micronutrients include, for example, acetyl L-carnitine in amounts of about 100 mg to 2000 mg, L-tyrosine in amounts of about 100 mg to 2000 mg, N-acetyl cysteine in amounts of about 100 mg to 2000 mg, and alpha-lipoic acid in amounts of about 50 mg to 1000 mg, and optionally L-taurine, in amounts of about 50 mg to 1000 mg. Other suitable amounts include acetyl L-carnitine in amounts of about 400 mg to 1600 mg, L-tyrosine in amounts of about 350 mg to 1400 mg, N-acetyl cysteine in amounts of about 250 mg to 1250 mg, and alpha-lipoic acid in amounts of about 150 mg to 600 mg; or acetyl L-carnitine in amounts of about 800 mg to 1200 mg, L-tyrosine in amounts of about 700 mg to 1500 mg, N-acetyl cysteine in amounts of about 500 mg to 750 mg, and alpha-lipoic acid in amounts of about 300 mg to 450 mg.

In another aspect, suitable amounts of micronutrients for single unit oral dosage forms include, for example, acetyl L-carnitine in amounts of about 100 mg to 150 mg, L-tyrosine in amounts of about 80 mg to 100 mg, N-acetyl cysteine in amounts of about 100 mg to 150 mg, alpha-lipoic acid in amounts of about 40 mg to 60 mg, and optionally L-taurine in amounts of about 40 mg to 60 mg. In another case, suitable dosage amounts include acetyl L-carnitine in amounts of about 90 mg to 190 mg, L-tyrosine in amounts of about 70 mg to 150 mg, N-acetyl cysteine in amounts of about 90 mg to 190 mg, and alpha-lipoic acid in amounts of about 35 mg to 75 mg; or acetyl L-carnitine in amounts of about 60 mg to 250 mg, L-tyrosine in amounts of about 50 mg to 200 mg, N-acetyl cysteine in amounts of about 60 mg to 250 mg, and alpha-lipoic acid in amounts of about 25 mg to 100 mg. Optional amounts of L-taurine for such dosage forms include, for example, 35 mg to 75 g, or 25 mg to 100 mg L-taurine.

Illustrative dosages of micronutrients for use herein also include, for example, acetyl L-carnitine in amounts of about 1 mg/day/kg to 27 mg/day/kg, L-tyrosine in amounts of about 1 mg/day/kg to 27 mg/day/kg, N-acetyl cysteine in amounts of about 1 mg/day/kg to 27 mg/day/kg, alpha-lipoic acid in amounts of about 0.5 mg/day/kg to 14 mg/day/kg, and optionally L-taurine, in amounts of about 0.5 mg/day/kg to 14 mg/day/kg. Other suitable dosages of micronutrients, include, for example, acetyl L-carnitine in amounts of about 5 mg/day/kg to 23 mg/day/kg, L-tyrosine in amounts of about 5 mg/day/kg to 20 mg/day/kg, N-acetyl cysteine in amounts of about 3 mg/day/kg to 18 mg/day/kg, and alpha-lipoic acid in amounts of about 2 mg/day/kg to 9 mg/day/kg; or acetyl L-carnitine in amounts of about 11 mg/day/kg to 18 mg/day/kg, L-tyrosine in amounts of about 10 mg/day/kg to 15 mg/day/kg, N-acetyl cysteine in amounts of about 7 mg/day/kg to 11 mg/day/kg, and alpha-lipoic acid in amounts of about 4 mg/day/kg to 7 mg/day/kg.

The nutrient compositions, together with a low dose CNS medication, may also be provided together with a general daily multivitamin and multimineral supplement, for example, as shown in Table 2 below.

TABLE 2

| ONE (1) Illustrative Tablet Contains: Typical Dosage Range: 1-8 tablets per day | | | |
|---|---|---|---|
| Antioxidant Amino Acids | | | |
| N-Acetyl Cysteine | 125 mg | | |
| Alpha Lipoic Acid | 50 mg | | |
| Stimulant Amino Acids | | | |
| Acetyl L-Carnitine | 125 mg | | |
| L-Tyrosine | 100 mg | | |
| Low-Dose Pharmaceutical Stimulant | | | |
| Methylphenidate USP | 2.5 mg | | |
| Optional Antioxidant Amino Acid | | | |
| L-Taurine | 50 mg | | |
| Optional Multivitamin Supp.: | | | |
| Beta-Carotene | 1,250 IU | Niacinamide | 7.5 mg |
| Vitamin C | 125 mg | Calcium Pantothenate | 7.5 mg |
| Vitamin E (total Vit. E) | 50 IU | Choline (Bitartrate) | 7.5 mg |
| Vitamin B-1 (Thiamine) | 7.5 mg | Inositol | 7.5 mg |
| Vitamin B-2 (Riboflavin) | 7.5 mg | Folic Acid | 100 mcg |
| Vitamin B-6 (Pyroxidine) | 15 mg | Biotin | 100 mcg |
| | | Vitamin D3 (Cholicalciferol) | 250 IU |
| | | Vitamin B12 (Methylcobalamin) | 250 mcg |
| Optional Multimineral Supp.: | | | |
| Calcium | 25 mg | Zinc | 3.75 mg |
| Magnesium | 12.5 mg | Selenium | 25 mcg |
| Iron | 2.25 mg | Chromium | 12.5 mcg |
| Iodine | 18.75 mcg | Molybdenum | 37.5 mcg |
| Copper | 0.25 mg | Potassium | 12.5 mg |
| Manganese | 1.25 mg | Boron | 0.25 mg |

As used herein, the term "nutrient" is intended to include either or both micronutrients and macronutrients. Micronutrients can include organic compounds or chemical elements required for biochemical and physiological processes. Such organic compounds and chemical elements may include, for example, vitamins, minerals, amino acids, antioxidants, cofactors, free radical scavengers, or other biochemical compounds that are utilized for the maintenance, regulation or function of biochemical and physiological processes. Macronutrients can include organic compounds and chemical elements which are required in relatively large amounts for biochemical and physiological processes of an animal. Specific examples of macronutrients include protein, carbohydrates, and fat.

The term "vitamin" herein means a micronutrient that acts generally in small amounts in the regulation of various metabolic processes but generally does not serve as an energy source or as a building unit. Vitamins are ordinarily ingested on a regular basis or stored in quantity in humans due to deficiencies in biosynthetic capacity. Specific examples of optional vitamin micronutrients that may be particularly useful together with the compositions and methods herein include vitamins A, B, C, D and E.

The term "mineral" herein means naturally occurring homogeneous or apparently homogeneous and generally solid crystalline chemical elements or compounds that result from inorganic processes of nature having a characteristic crystal structure and chemical composition. Specific examples of optional mineral and chemical element micronutrients that may be particularly useful together with the compositions and methods herein include zinc, selenium, iron, iodine and boron.

The term "antioxidant" herein means a substance that opposes oxidation or inhibits reactions promoted by, for example, oxygen, peroxides, or free radicals. Specific examples of additional antioxidant micronutrients useful together with the compositions and methods herein include vitamin C, bioflavonoid complex, vitamin E, vitamin B6, and beta-carotene. Specific examples of cofactor micronutrients useful together with the compositions and methods herein include vitamin B1, vitamin B2 and vitamin B6.

As used herein, the term "high potency" when used in reference to an antioxidant is intended to mean a non-vitamin or non-mineral antioxidant. The chemical or medicinal strength or the efficacy of such high potency antioxidants in the compositions herein can be, for example, greater in reducing oxidation, free radical destruction or chemical reactions induced by these chemical species, as compared to other antioxidants, or as compared to an amount of these same antioxidants as they are normally found in food. The chemical efficacy of the high potency antioxidants as they are used in the nutrient component herein is due to, for example, greater molar amounts of antioxidants or enhanced antioxidant effectiveness resulting from cooperative combinations with other antioxidants or nutrients in the formulations herein. The preferred high potency micronutrient antioxidants for use herein are N-acetyl cysteine and alpha lipoic acid. Examples of additional high potency antioxidants for use herein include L-taurine, coenzyme Q10, and/or glutathione.

The term "therapeutically effective amount" of a composition or component thereof refers to an amount that is effective for an intended therapeutic purpose. For example, in the context of treating chronic fatigue, a "therapeutically effective amount" is any amount that is effective in producing a significant positive effect on individuals suffering from chronic fatigue, as demonstrated by the Example below. With regard to the CNS component of the disclosed compositions and methods, a "therapeutically effective amount" is a low dosage amount as defined hereinabove, or any amount sufficient to induce patient stimulation of energy production without undue side effects when administered together with therapeutically effective amounts of the micronutrient stimulant and micronutrient antioxidant components, as disclosed herein. With regard to the micronutrient stimulants disclosed herein, a "therapeutically effective amount" is any amount sufficient to achieve patient stimulation of energy production either alone or when administered together with therapeutically effective amounts of the CNS medicament and micronutrient antioxidant components, as disclosed herein. In the context of micronutrient antioxidants, a "therapeutically effective amount" is any amount sufficient to provide a decrease in free radicals and oxidative stress either alone or when administered in combination with therapeutically effective amounts of the CNS medicament and micronutrient stimulant components, as disclosed herein.

Illustrative examples of therapeutically effective amounts are shown in Table 2 and the Example below. Therapeutically effective amounts of nutrients and CNS medications can also vary in range from the exemplary oral dosages shown herein by about 25% of the shown dosages up to and greater than about 200% of the dosages shown. In one case, the starting dosage may be 4 pills per day taken as 2 pills 2×/day—each pill having the nutrient composition shown in Table 2 and a corresponding low dosage amount of the daily CNS medication shown in Table 1. However, in patients who are extremely sensitive to taking prescription drugs or nutritional supplements, the effective dosage may be as low as one pill per day. For patients who do not respond to the starting dosage within 1-2 weeks, an increase in the treatment dosage may then be made to 6 pills per day (taken as 3 pill 2×/day) and, if necessary, to 8 pills per day (taken as 4 pills 2×/day—each pill having the composition shown in Table 2). Therefore, therapeutically effective amounts for oral dosages of one or more of the nutrients shown in Table 2 can be, for example, 30, 40, 50, 60, 70, 80, 90, 110, 120, 130, 140, 150, 160, 170, 180, 190 or greater than 200% of the amounts shown in Table 2. Effective amounts other than those exemplified above can be determined by those skilled in the art given the teachings and guidance provided herein.

In one case, the micronutrient components may further include a daily multivitamin/mineral supplement, which may be, for example, as shown in aspects of Table 2 above. Thus, the nutrient components may include a combination of vitamins, minerals, and high potency antioxidants. The nutrient components may include a combination of vitamin and mineral antioxidants, vitamin and high potency antioxidants, or mineral and high potency antioxidants. The nutrient components also may include various other combinations of these antioxidants and may contain, for example, one, two, three, four, five or more different antioxidants. Antioxidants are beneficial to physiological processes because they augment immune strength or physiological detoxification functions within cells and tissues. Moreover, multinutrient combinations are beneficial physiologically because of their interdependence in a variety of cellular processes. For example, mammalian mitochondria are interdependent on multiple nutrients for healthful and efficient functioning. Administration of multinutrient antioxidant formulations can improve the functions dependent on such antioxidants as well as improve the functions dependent on the interplay of antioxidants with other nutrients such as vitamins and minerals. In some aspects, combinations of nutrients included as the nutrient compositions herein may include amounts or types of nutrients that together support the interdependent roles of two or more nutrients. A specific example of such interdependence is the ability of Vitamin C (ascorbate) to regenerate native Vitamin E (tocopherol) from its oxidized state as well as alpha lipoic acid to regenerate native Vitamin C (ascorbate) from its oxidized state.

N-acetyl-cysteine (NAC) is a nutrient with potent antioxidant activity. The acetyl moiety of the amino acid cysteine is a prevalent bioavailable oral source of glutathione. Glutathione is a potent antioxidant and component of the glutathione peroxidase enzyme system.

Alpha lipoic acid is a potent antioxidant found, for example, in the mitochondria. It acts as a coenzyme in the alpha-keto-dehydrogenase enzyme complex of the Kreb's cycle to facilitate aerobic respiration as well as participates in the metabolic pathways which regenerate de novo levels of ascorbate, alpha-tocopherol, and glutathione. Alpha lipoic acid also functions as a potent free radical scavenger in both hydrophilic and hydrophobic cellular compartments.

Acetyl-L-carnitine is a stimulant nutrient (amino acid). It enriches the fuel mixture of the mitochondria. The acetyl moiety of the amino acid carnitine regulates fatty acid transport across the mitochondrial membrane. It enhances mitochondrial function and energy production by transporting additional fuel stores into the mitochondria during times of stress. It also functions to provide the mitochondria with a fuel source that enhances its ability to produce energy under anaerobic conditions. Anaerobic metabolism can occur, for example, when the electron transport chain is dysregulated due to a depletion of mitochondrial DNA.

L-tyrosine is one of the 20 amino acids that are used by cells to synthesize proteins. Tyrosine phosphorylation is considered to be one of the key steps in signal transduction and regulation of enzymatic activity. L-tyrosine is also a precursor to norepinephrine, a neurotransmitter that exerts a potent stimulating effect on the central nervous and endocrine systems.

Vitamin antioxidants that can be selected for inclusion in the micronutrient component herein include, for example, beta-carotene, vitamin C, vitamin E, vitamin B6 or vitamin B12. One or more of these or optional vitamin antioxidants can be included in the micronutrient component of the disclosed embodiments.

Beta-carotene is a vitamin antioxidant that also is convertible to vitamin A in the liver of animals. This class of nutrients includes all those defined by the term "retinoids" and includes those described as retinols. Since Vitamin A is only found in animal foods, beta-carotene provides about two thirds of the daily intake of retinoids in humans. Beta-carotene is converted to Vitamin A in both the gastrointestinal tract and the liver. Vitamin A is used by the body to enhance retinal function and night vision and also plays a role in the formation and maintenance of healthy epithelial tissue, which forms the body's primary barrier to infection.

Vitamin C, or ascorbic acid or ascorbate, is a strong reducing agent that can be reversibly oxidized to dehydroascorbic acid. The term vitamin C, as it is used herein, is intended to include any of several enolic lactones of keto aldonic acids that are stereoisomers of ascorbic acid. As described above, vitamin C functions in, for example, the Kreb's cycle and a deficiency can lead to scurvy. Vitamin C also functions in building and maintaining bone matrix, cartilage, dentin, collagen, and connective tissue in general. Furthermore, Vitamin C participates in resistance to infection by the immune system and proper adrenal gland function in reaction or resistance to stress.

Vitamin E, found in nature as mixed tocopherols, is a fat-soluble tocopherol complex with antioxidant properties. Vitamin E also plays a role in protecting cellular membrane fatty acids from oxidative damage. It is nutritionally required for mammals in which its absence is associated with infertility, muscular dystrophy, or abnormalities in the vascular system. The term vitamin E, as it is used herein, is intended to include, any of the structurally similar chemical compounds found within the tocopherol family of organic compounds.

Vitamin B6, or pyroxidine HCl or pyridoxine, is a water-soluble component of the vitamin B complex and plays a role in the proper formation and health of red blood cells and blood vessels, nerve function, gums, and teeth. In its active form, pyridoxalphosphate ($B6-PO_4$) is a coenzyme involved in many types of transamination (amino acid metabolism) and decarboxylation reactions occurring in amino acid, carbohydrate, and fat metabolism. Vitamin B6 also is a cofactor in immune system functioning. Although not generally considered to be an antioxidant, vitamin B6 does exhibit antioxidant properties.

Vitamin B 12 (along with choline and folic acid) is a nutritional factor involved in transmethylation reactions. Vitamin B 12 is involved in the production of red blood cells and healthy nervous system functioning.

Mineral antioxidants that can be optionally selected for inclusion in the nutrient component herein include, for example, zinc or selenium. Either or both of these minerals as well as vitamin antioxidants may optionally be included in the micronutrient component of the disclosed embodiments.

Zinc, taken in the form of picolinate, carbonate, ascorbate, or complexed to a chelated amino acid, for example, is one mineral exhibiting antioxidant activity. Zinc also is utilized for the metabolic activity of about 200 or more enzymes and is considered important for cell division and the synthesis of DNA and polypeptides. Zinc deficiency contributes to growth retardation; even mild deficiency may limit growth in otherwise healthy children. Zinc functions, for example, in energy metabolism as part of the lactate dehydrogenase enzyme system. Zinc also participates in immune function, as evidenced by its role in promoting enhanced wound healing, and serves as an antioxidant as part of the superoxide dismutase enzyme system.

Selenium, taken in the form of picolinate, carbonate, ascorbate, or complexed to a chelated amino acid for example, is another mineral having antioxidant activity. Selenium is a component of the active sites of, for example, the enzymes glutathione peroxidase, iodothyronine 5'-deiodinase, and mammalian thioredoxin reductase. It is also present in several other mammalian selenoproteins. Both glutathione peroxidase and thioredoxin reductase catalyze reactions involved in the protection of cellular components against oxidative and free radical damage. Therefore, selenium as well as zinc augments the activity of enzymes within one or more antioxidant enzyme systems of an individual. Selenium also plays a role as a mammalian cell's second line of defense against damaging cell peroxides. It performs this role as an integral part of the glutathione peroxidase enzyme system.

Any of the nutrient antioxidants described above as well as others known in the art can optionally be included in the nutrient component of the compositions and methods herein. Additionally, other nutrients that function, for example, in one or more of the antioxidant enzyme systems described above or others also can be included.

Additional vitamins or minerals that can be included in the compositions and treatment regimes herein include additional vitamins, such as mixed tocopherols, vitamin B1 (thiamine), vitamin B2 (riboflavin), niacinamide, calcium pantothenate, choline (bitartrate), inositol, folic acid (folacin), biotin, or vitamin D3 (cholicalciferol), and/or additional minerals, such as calcium, magnesium, iron, iodine, copper, manganese, potassium, chromium, molybdenum, or boron. For example, one or more nutrients from the vitamin category can be additionally included. Similarly, one or more nutrients from the mineral category can be additionally included. Alternatively, one or more nutrients from both the vitamin and the mineral categories can be additionally included in the micronutrient component of the disclosed embodiments. Therefore, the micronutrient component of the disclosed embodiments can include any one or more, as well as all of the various combinations of the following vitamins or minerals: beta-carotene, vitamin C, vitamin E, vitamin B6, vitamin B 12, zinc, selenium, mixed tocopherols, vitamin B1 (thiamine), vitamin B2 (riboflavin), niacinamide, calcium pantothenate, choline (bitartrate), inositol, folic acid (folacin), biotin, vitamin D3 (cholicalciferol), calcium, magnesium, iron, iodine, copper, manganese, potassium, chromium, molybdenum, and/or boron.

Calcium is present in large amounts in the human body and is needed, for example, for structural integrity, blood clotting and nerve cell functioning. Calcium also is a mineral that is supportive and balancing to the nervous system and thus is particularly useful in some aspects of the compositions and methods disclosed herein.

Magnesium is involved in healthy intracellular metabolism of macromolecules such as carbohydrates and protein. A magnesium-ATP complex is the form of ATP used as a substrate in many biochemical reactions. Magnesium is a mineral that is supportive and balancing to the nervous system and thus is particularly useful in some aspects of the compositions and methods disclosed herein.

In another aspect, the present disclosure provides a pharmaceutical composition containing a combination of nutrients and/or one or more CNS medicaments, and optionally a pharmaceutically acceptable carrier. The compositions can be prepared by conventional methods known in the art. The term "pharmaceutically acceptable carrier" refers to any inactive substance that is suitable for use in a formulation for the delivery of the CNS stimulant and/or nutrients. A carrier may be an antiadherent, binder, coating, disintegrant, filler or diluent, preservative (such as antioxidant, antibacterial, or antifungal agent), sweetener, absorption delaying agent, wetting agent, emulsifying agent, buffer, and the like.

The pharmaceutical compositions may be in any suitable form, such as liquid, semi-solid, and solid dosage forms. Examples of liquid dosage forms include solution (e.g., injectable and infusible solutions), microemulsion, liposome, dispersion, or suspension. Examples of solid dosage forms include tablet, pill, capsule, microcapsule, and powder. A particular form of the composition suitable for delivering a CNS stimulant and nutrient compositions is a solid dosage form, such as a pill.

The compositions can be administered via any suitable enteral route or parenteral route of administration. Examples of enteral routes include oral, mucosal, buccal, and rectal route, or intragastric route. Examples of parenteral routes of administration include intravenous, intramuscular; intradermal, intraperitoneal, transtracheal, epidural and intrasternal, subcutaneous, or topical administration. The compositions can be administered using any suitable method, such as by oral ingestion, nasogastric tube, injection, infusion, implantable infusion pump, and osmotic pump.

In a preferred embodiment, the low-dose CNS stimulant medication and nutrient components are combined in a unit dosage form for oral ingestion (such as a pill, tablet, capsule, or liquid) in order to provide a safe and effective treatment. There is an intimate relationship between the medication and the nutrients, as the above-described dosing relationship between the key micronutrients (at least acetyl L-carnitine, L-tyrosine, N-acetyl cysteine, and alpha lipoic acid) and the CNS medication is beneficial to the success of the treatment. Thus, the CNS stimulant medication and nutrient compositions may be provided together in a single dosage form. This single dosage form ensures that patients are receiving the proper ratio of the nutrient compositions and the CNS medication. Thus, the CNS and nutrient components may be formulated as separate tablets or, more preferably, as a unitary combination tablet. The preferred pharmaceutical formulations are solid compositions, particularly tablets and hard-filled or liquid-filled capsules. Oral administration of the components is preferred. According to some aspects, patients may take, for example, from one to eight tablets per day as shown in Table 2, depending on their response to the treatment. In any event, in most instances, the CNS medication will be provided in daily low dosage amounts. The dosage forms may be administered once per day, twice, or multiple times per day, and continuing over a treatment period until symptoms disappear and/or significantly subside, typically 4 weeks, 8 weeks or 12 weeks, but also may continue as a prophylactic measure in the long term after symptoms have disappeared or significantly subsided, as determined by the attending physician.

While, in one case, a starting dosage for treatment of patients having CFS may be 2 tablets (Table 2), for example, twice per day, based on each particular patient's response the dosage also may be changed, for example, to 4 pills, twice per day or to 1 pill, twice per day. It is to be understood that for any particular subject, specific dosage regimens should be adjusted over time according to the individual need and the professional judgment of the practitioner supervising administration of the compositions. Thus, while a patient may be started at one dose, that dose may be varied over time as the patient's condition changes.

The term "daily" means that the dosage is to be administered at least once daily. The frequency may be once daily, but also may be more than once daily, provided that any specified daily dosage is not exceeded.

The term "combination" means that the daily dosage of each of the CNS and the nutrient components is administered during the treatment day. As indicated above, it is particularly preferred that the components of the combination are administered at the same time; either as a unitary dosage form containing both components, or as separate dosage units. The components of the combination also may be administered at different times during the day, provided that the desired daily dosage is achieved.

In one aspect, it is preferable that there is no break in the treatment regimen during the treatment period. Thus, "continuous administration" of the CNS and nutrient combination means that the combination is administered at least once daily during the entire treatment period. Treatment periods may vary depending on the symptoms to be treated. Physician evaluation along with patient interaction will assist the determination of the duration of treatment. The dosage regimen may be indefinite, long term, short term, or treatments of a finite term, that may be less than 12 weeks, 8 weeks, or less than 4 weeks. It is anticipated that a patient may miss, or forget to take, one or a few dosages during the course of a treatment regimen, however, such patient is still considered to be receiving continuous administration.

Efficacy of the nutrient component correlates with purity level of the nutrients. Higher purity levels yield greater activity and, consequently, can allow a reduction in the amount included in one or more administrations.

The CNS medication and nutrients used with the compositions and methods herein preferably have a purity level greater than about 90%, more preferably greater than about 95%, and most preferably greater than about 98%. These higher purity levels can be obtained by methods well known in the art. Additionally, purity levels greater than about 98% and particularly greater than about 99% by total weight can be obtained by omitting fillers, binders or lubricants such as stearates or palmitates. Additionally, other substances which are known in the art to inhibit, or possibly inhibit, the absorption, bioavailability or tolerance of compounds in individuals also can be excluded from the formulations to achieve greater than about 98-99% purity without compromising the activity of the micronutrient component. However, it should be understood that such fillers, binders, lubricants or other substances also can be included when desirable. Given the teachings and guidance provided herein, those skilled in the art will know whether to utilize nutrient compositions less than the purity levels described above or to include additional substances and pharmaceutically acceptable excipients in a formulation. Accordingly, various formulations of pharmaceutically acceptable carriers known in the art for packaging and administration of nutrients or other administrable chemical compounds can be utilized in conjunction with the disclosed embodiments.

Nutrients for use in the formulations herein can be obtained from any of various sources known to those skilled in the art. For example, individual nutrients or combinations meeting the amounts or dosages exemplified herein can be produced by a commercial manufacturer. An exemplary commercial manufacturer is Enzymatic Therapy (Green Bay Wis., and which can be found at the URL enzymatictherapy.com). Additionally, the nutrients can be purified biochemically or synthesized chemically using methods known to those skilled in the art.

The following example is intended to be illustrative and not limiting. Other CNS stimulants or combinations thereof may be used, as well as modifications of the dosing schedule and duration, and/or use of fewer or additional micronutrients, multivitamins and minerals, to maintain the appropriate standard of care for each set of patient chronic fatigue circumstances.

EXAMPLE

A Phase IIa clinical trial was performed in Mill Valley, Calif. The results of this prospective, open-label 12-week clinical trial strongly demonstrated a significant positive effect on individuals suffering from chronic fatigue.

Objective: To investigate the effects of a nutrient-drug hybrid treatment utilizing a low-dose amphetamine derivative combined with a highly potent combination of micronutrients on fatigue, concentration disturbances, and quality of life in patients with Chronic Fatigue Syndrome (CFS).

Study design: A prospective, open label 12-week clinical trial in 15 patients who fulfill the 1994 CDC criteria for Chronic Fatigue Syndrome and have concentration difficulties. Study duration: 12 weeks. Eligibility criteria: The main eligibility criteria were male or female subjects who fulfill the 1994 CDC case definition for CFS, 18 to 65 years of age, and had subjective complaints of alertness and/or concentration deficits.

Study intervention: Oral treatment was provided to 15 CFS patients consisting of a nutrient-drug hybrid containing the nutrients and dosages listed in Table 2 except that the methylphenidate and nutrients were delivered as separate pills. Treatment commenced with an initial dosage of 4 nutrient pills, plus methylphenidate 10 mg taken 1×/day. After 3 days of treatment, the study patients were contacted and, if they were tolerating the treatment without difficulty, the treatment dosage was increased to 4 nutrient pills, plus methylphenidate 10 mg taken 2×/day. This dosage represents the nutrient and methylphenidate dosages shown in Table 2 which corresponds to a total of 8 pills per day (4 pills taken 2×/day).

The study treatment used the composition shown in Table 2, which includes the CNS medication, the four key nutrients, and a broad-spectrum multivitamin/mineral supplement to maintain patient standard of care (study patients had previously agreed not to ingest any supplemental nutrients, vitamins, or minerals, other than those provided during the study).

The primary outcome objective for this study was a clinically significant improvement in at least half the CFS patients. Clinically significant improvement is defined for the purposes of this study as an improvement of ≥33% in either of the fatigue primary outcome measures. To date, no CFS treatment has shown this level of benefit.

Primary outcome measures: Three instruments were used to assess fatigue and concentration in accordance with established measurement techniques. See, e.g., Blockmans, D., et al., "Does Methylphenidate Reduce the Symptoms of Chronic Fatigue Syndrome?" Am. J. of Medicine (2006) 119, 167.e23-167.e30.

Two instruments were used to assess change in fatigue: (1) The Checklist Individual Strength (CIS) is a self-report questionnaire that assesses the severity of fatigue over the previous 2 weeks, ranking from 20 to 140. For the purposes of this study, we defined a clinically significant response as a 33% fall in fatigue scores or a score on the CIS ≤76, which has been defined previously as the cut-off point for probable fatigue in employees. Patients fulfilling these criteria were considered responders. (2) A Visual Analogue Scale (VAS) measuring subjective fatigue was used as a second instrument (range 0 to 10).

Concentration disturbances were assessed with the concentration subscale of the CIS (5 items, range 5-35) on the one hand, and with a VAS (range 0-10) measuring subjective concentration on the other hand. Analogous to the CIS total score, significant clinical improvement was defined as a 33% fall of the concentration disturbance score on the CIS subscale.

Figure 2:
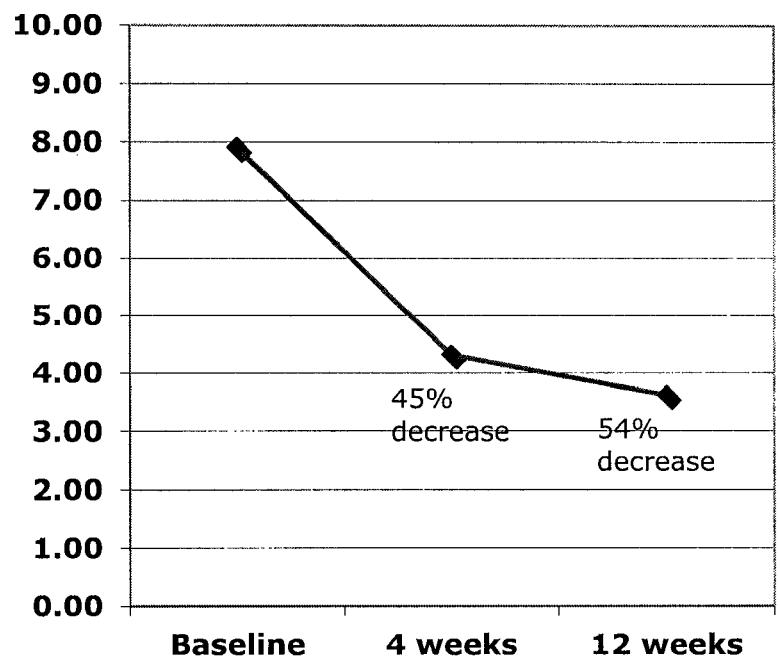
FIG. 2 illustrates patient fatigue as measured by Visual Analogue Scale (VAS) over time according to one aspect of the compositions and methods disclosed herein.

Study Results—Primary Outcome Measures:

Fatigue: At the 4-week interim analysis, a clinically significant reduction in fatigue, as measured by a 33% or greater fall in the total CIS score, was present in 66% of the participants [10 of 15 responded significantly] with a mean fatigue symptom reduction of 33%. At the interim 12-week analysis, a clinically significant reduction in fatigue, as measured by a 33% or greater fall in the total CIS score, was present in 100% of the participants [7 of 7 patients responded significantly] with a mean fatigue symptom reduction of 41% (see FIG. 1). The Visual Analogue Scale (VAS) showed similar results that were consistent with a clinically significant reduction in fatigue symptoms in 66% of the study patients [10 of 15 responded significantly] with a mean fatigue symptom reduction of 54% at 12-weeks (see FIG. 2).

Figure 3:
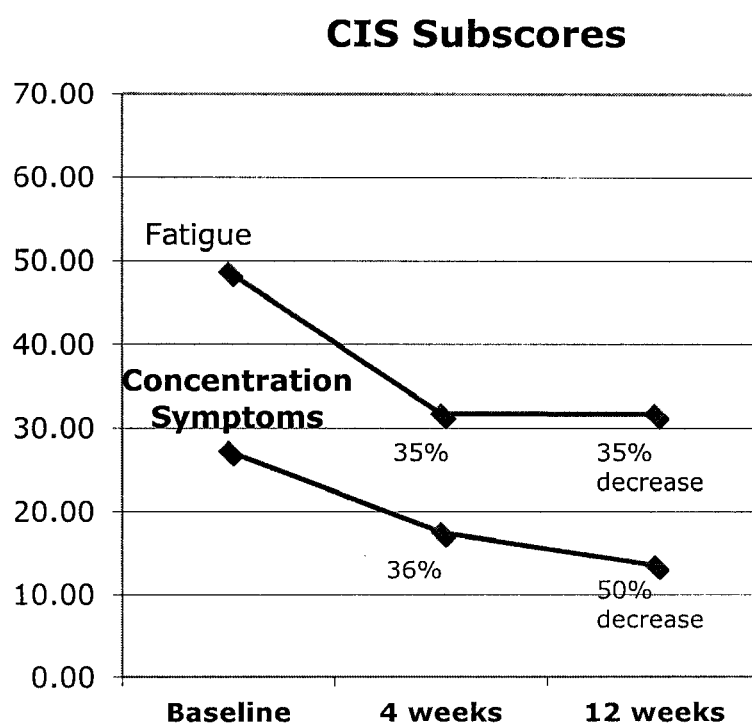
FIG. 3 illustrates patient fatigue and concentration disturbance as measured by CIS over time according to one aspect of the compositions and methods disclosed herein.
Figure 4:
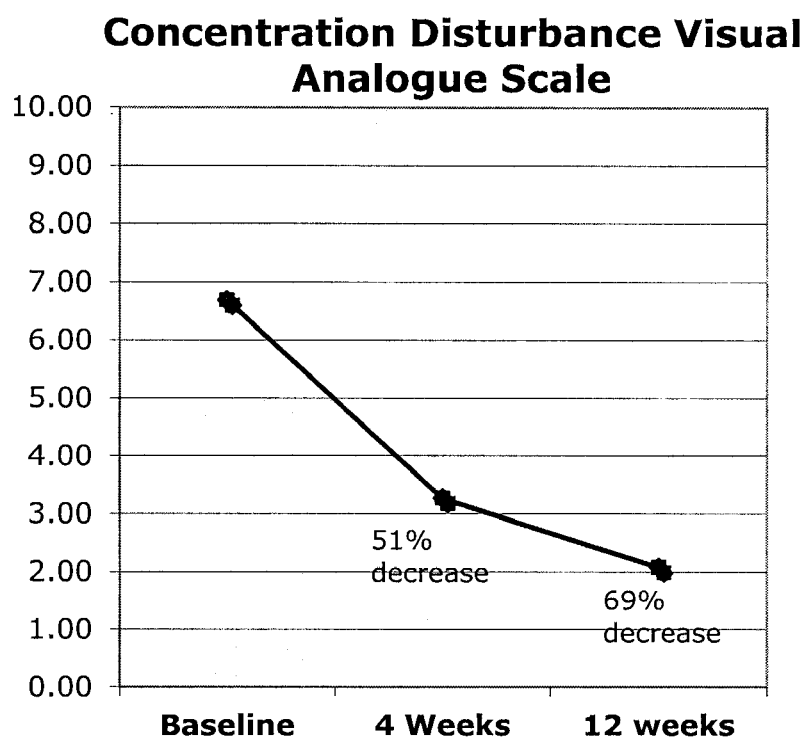
FIG. 4 illustrates patient concentration disturbance as measured by VAS over time according to one aspect of the compositions and methods disclosed herein.

Concentration disturbances: At the 4-week interim analysis, a clinically significant reduction in concentration disturbances, as measured by a 33% or greater fall in the concentration subscore of the CIS, was present in 66% of the participants [10 of 15 responded significantly] with a mean reduction in concentration disturbance symptoms of 36%. At the 12-week analysis, a clinically significant reduction in concentration disturbance symptoms, as measured by a 33% or greater fall in the concentration subscore of the CIS, was present in 85% of the participants [6 of 7 patients responded significantly] with a mean reduction in concentration disturbance symptoms of 50% at 12-weeks (see FIG. 3). The Visual Analogue Scale (VAS) showed similar results that were consistent with a clinically significant reduction in concentration disturbance symptoms in 80% of the study patients [12 of 15 responded significantly] with a mean reduction of concentration disturbance symptoms of 54% at 12-weeks (see FIG. 4).

Conclusions: Treatment with the nutrient-drug combination and method described herein significantly improves fatigue, alertness, and concentration disturbances in a majority of CFS patients. The nutrient-drug hybrid treatment used in this study was effective and well-tolerated in treating fatigue and concentration disturbances associated with Chronic Fatigue Syndrome.

All patents and publications cited herein are incorporated herein by reference. It should be readily understood that the invention is not limited to the specific examples and embodiments described and illustrated above. Rather, the examples and embodiments can be modified to incorporate any number of CNS drugs, nutrient components, dosing techniques and other variations, alterations, substitutions or equivalent arrangements not heretofore described, which are commensurate with the spirit and scope of the invention. For example, although the examples have been described with regard to certain preferred embodiments for carrying out the invention with regard to the treatment of CFS using low dose methylphenidate, the invention may also be used for preparing compositions and treatment of chronic fatigue with other CNS drugs, as well as treatment of other chronic fatigue conditions. Accordingly, the invention is not limited by the foregoing description, but is only limited by the scope of the appended claims.

I claim:

1. A method for treating chronic fatigue in a human patient comprising:
   administering a daily dosage of about 2.5 to 40 mg methylphenidate; and
   administering daily about 100 to 2000 mg acetyl L-carnitine,
   about 100 to 2000 mg L-tyrosine,
   about 100 to 2000 mg N-acetyl cysteine, and
   about 50 to 1000 mg alpha lipoic acid.
2. The method of claim 1, wherein acetyl L-carnitine is administered in a Range of about 400 to 1600 mg/d.
3. The method of claim 1, wherein L-tyrosine is administered In a range of about 350 to 1400 mg/d.
4. The method of claim 1, wherein N-acetyl cysteine is administered in a range of about 250 to 1250 mg/d.
5. The method of claim 1, wherein alpha-lipoic acid is administered in a range of about 150 to 600 mg/d.
6. The method of claim 1, wherein said administering is conducted on a continuous basis for at least 12 weeks.
7. The method of claim 1, wherein the chronic fatigue is associated with Chronic Fatigue Syndrome.
8. The method of claim 1, wherein the chronic fatigue is associated with fibromyalgia.
9. The method of claim 1, wherein the chronic fatigue is associated with a condition selected from the group of cancer, HIV/AIDS, chronic hepatitis B & C, autoimmune disorders, Lyme's disease, Parkinson's disease, Alzheimer's disease, depression, ADD, ADHD, multiple sclerosis, sickle cell anemia, and congestive heart failure.
10. The method of claim 1, wherein the methylphenidate, acetyl L-carnitine, L-tyrosine, N-acetyl cysteine, and alpha lipoic acid are orally administered together in a combined dosage form.
11. The method of claim 1, wherein the methylphenidate comprises methylphenidate HCl.
12. The method of claim 1, wherein the methylphenidate is administered in an amount of about 5 to 40 mg/day.
13. The method of claim 1, wherein the methylphenidate is administered in an amount less than 20 mg/day.

* * * * *